United States Patent
Dang et al.

(10) Patent No.: US 8,770,039 B2
(45) Date of Patent: Jul. 8, 2014

(54) LOAD MONITORING ARRANGEMENT FOR CHAIN SUPPORT

(75) Inventors: Quoc Anh Dang, Houston, TX (US); David Seaman, Waller, TX (US)

(73) Assignee: SOFEC, Inc., Houston, TX (US)

( * ) Notice: Subject to any disclaimer, the term of this patent is extended or adjusted under 35 U.S.C. 154(b) by 476 days.

(21) Appl. No.: 13/113,653

(22) Filed: May 23, 2011

(65) Prior Publication Data

US 2012/0297890 A1    Nov. 29, 2012

(51) Int. Cl.
   *G01N 3/08* (2006.01)
(52) U.S. Cl.
   USPC .......................................................... 73/828
(58) Field of Classification Search
   USPC .......................................................... 73/828
   See application file for complete search history.

(56) References Cited

U.S. PATENT DOCUMENTS

| | | | |
|---|---|---|---|
| 3,992,934 A * | 11/1976 | Clark | 73/862.631 |
| 5,745,042 A * | 4/1998 | Pratt | 340/657 |
| 5,809,925 A * | 9/1998 | Montgomery | 114/200 |
| 5,845,893 A | 12/1998 | Groves | |
| 6,663,320 B1 | 12/2003 | Braud et al. | |
| 6,925,890 B2 | 8/2005 | Fontenot | |
| 7,240,633 B2 * | 7/2007 | Barlow | 114/200 |
| 7,325,508 B2 * | 2/2008 | Boatman et al. | 114/230.2 |
| 7,926,436 B2 * | 4/2011 | Boatman et al. | 114/230.2 |

* cited by examiner

*Primary Examiner* — Lisa Caputo
*Assistant Examiner* — Octavia D. Hollington
(74) *Attorney, Agent, or Firm* — Gary L. Bush; Andrews Kurth LLP (57) ABSTRACT

An arrangement for measuring tension in mooring chains 38 connected to a floating structure 6. The arrangement includes a chain stopper 12 having a first portion 16 and a second portion 18. The first portion 16 has a first load bearing surface 42 and the second portion 18 has a second load bearing surface 50. The arrangement further includes at least one pin 14 arranged and designed for measuring shear loads and laterally traversing the chain stopper 12 between the first and second load bearing surfaces 50, 42, whereby, upon application of a load to the chainstopper assembly 12, the at least one pin 14 is positioned in the load path.

20 Claims, 7 Drawing Sheets

LOAD MONITORING ARRANGEMENT FOR CHAIN SUPPORT

BACKGROUND OF THE INVENTION

1. Field of the Invention

The invention relates generally to measuring tension in mooring chains in marine applications. More particularly, the invention relates to measuring the tension in anchor chains for use in mooring FPSO vessels.

2. Description of the Prior Art

Floating, production, storage, and offloading (FPSO) vessels include a mooring system that requires measurement of tension in mooring chains for proper installation and for management of loads during operation. FPSOs are often subject to harsh environments and have long service lives requiring that tension measurement components of the mooring system be robust. The design lifetime of an FPSO and its measuring system may exceed 20 years.

Prior art methods for measuring loads in mooring chains have included placing strain gages on the housing of a chainstopper. This arrangement is disadvantageous, because the strain gages are often mounted in an exposed location, subjecting the strain gages to harsh environments. Furthermore, strain gages in this arrangement are difficult to replace, and to recalibrate after replacement.

Alternatively, load cells have been placed directly on a chain link to measure load in the chain when mooring an offshore structure such as an offshore vessel. U.S. Pat. No. 5,845,893 discloses an extensiometer mounted on a latch housing to measure chain force in an anchor chain when it is held by a latch mechanism.

Another prior art method for measuring a load in a mooring chain places a non-contact sensor into the interior of a trunnion block to measure the deflection of the upper and lower trunnions. U.S. Pat. No. 6,925,890 discloses the placement of a non-contact sensor on a trunnion block.

3. Identification of Objects of the Invention

A primary object of the invention is to provide a system for measuring tension in mooring chains that overcomes the disadvantages of the prior art.

Another object of the invention is to provide a system and method for measuring tension in marine mooring chains that achieves reduced maintenance and increased reliability;

Another object of the invention is to provide a system and method for measuring tension in mooring chains that places a tension measuring instrument directly in the load path of the mooring chain;

Still another object of the invention is to provide a system and method for measuring tension in mooring chains with a tension measuring instrument that can be more easily calibrated off-site, prior to installation on the mooring chain.

SUMMARY OF THE INVENTION

The objects identified above, along with other features and advantages of the invention, are incorporated in an arrangement for determining the tension in a mooring chain by measuring the reactive load in structures that support the chain. One aspect of the invention provides, for example, a chainstopper having a pair of pins extending laterally therethrough. The chainstopper includes two load carrying components, which, when combined with the pins, carry the load of the mooring chain in a path directly through the pins. The pins in turn have strain gages for measuring the load applied to the pins, thereby providing a measurement of the tension in the mooring chain associated with the particular chainstopper.

The invention further includes anti-lift keys connecting the load carrying components and restricting movement of one component relative to the other.

An alternative embodiment of the invention provides a method of measuring the tension in a mooring chain. The method includes providing a chainstopper assembly configured to connect a mooring chain to a vessel. The chainstopper assembly has at least two load bearing members with pins positioned therebetween so that the load applied to the chain stopper assembly passes through the pins. The method also includes calibrating the pins prior to installation in the chainstopper assembly.

BRIEF DESCRIPTION OF THE DRAWINGS

The invention will be better understood by reading the detailed description of embodiments which follow and by examining the accompanying drawings, in which.

DESCRIPTION OF A PREFERRED EMBODIMENT OF THE INVENTION

The aspects, features, and advantages of the invention mentioned above are described in more detail by reference to the drawings wherein like reference numerals represent like elements.

Figure 1:
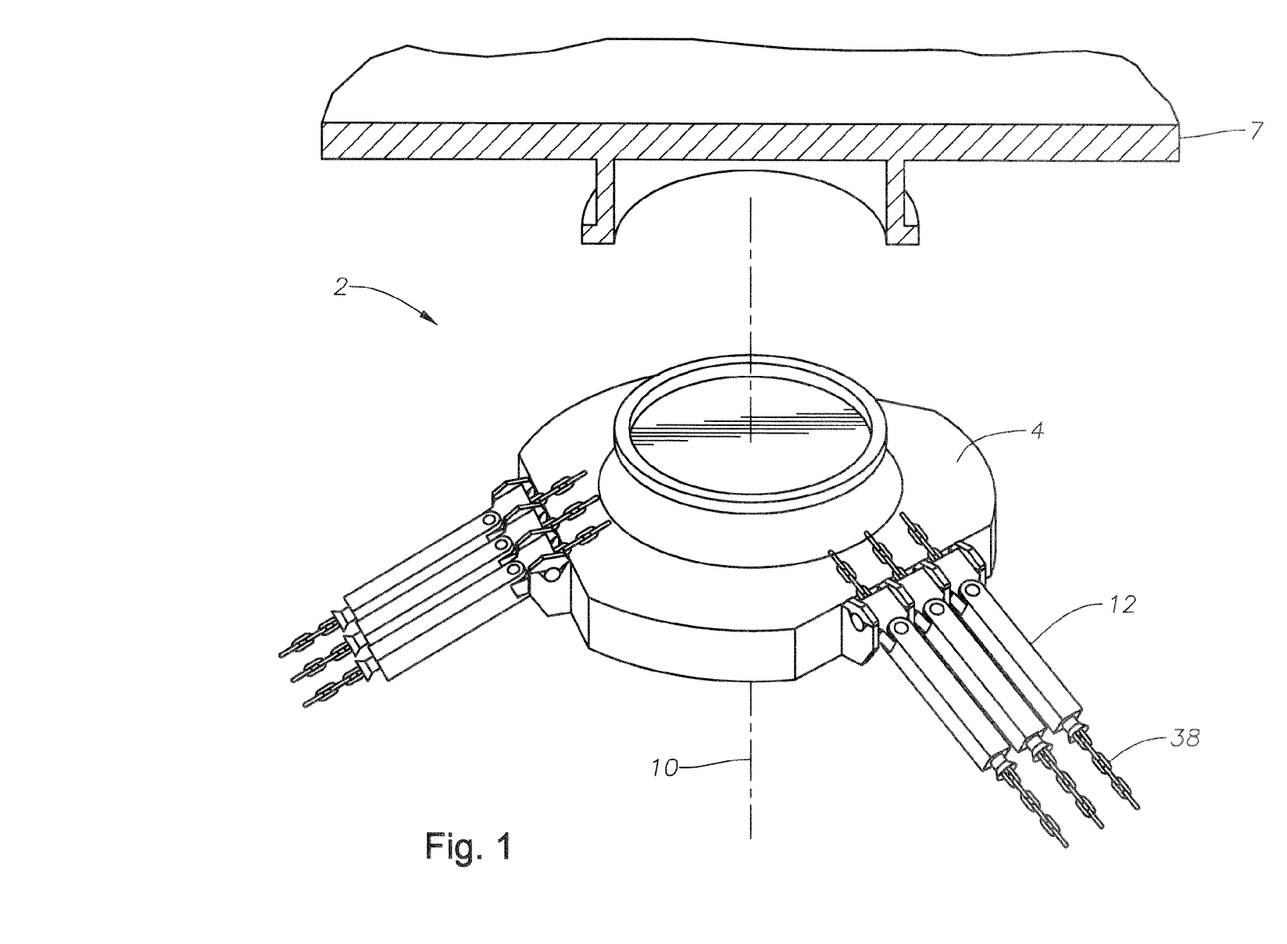
FIG. 1 is a perspective view of a mooring system including mooring chains arranged in groups of three with each mooring chain connected to a chain stopper according to the invention.

FIG. 1 shows a mooring system 2 including a chaintable 4 rotatably connectable to a vessel 7 and to mooring chains 38. When connected to the chaintable 4, the vessel 7 is free to weathervane about a vertical axis 10. The upper end of each mooring chain 38 is attached to the chaintable 4 via a chainstopper assembly 12 embodying the invention. Each chainstopper assembly 12 includes pins 14 (shown in FIG. 2) arranged and designed to measure the load in the mooring chain 38 associated with the chainstopper assembly 12.

Figure 3:
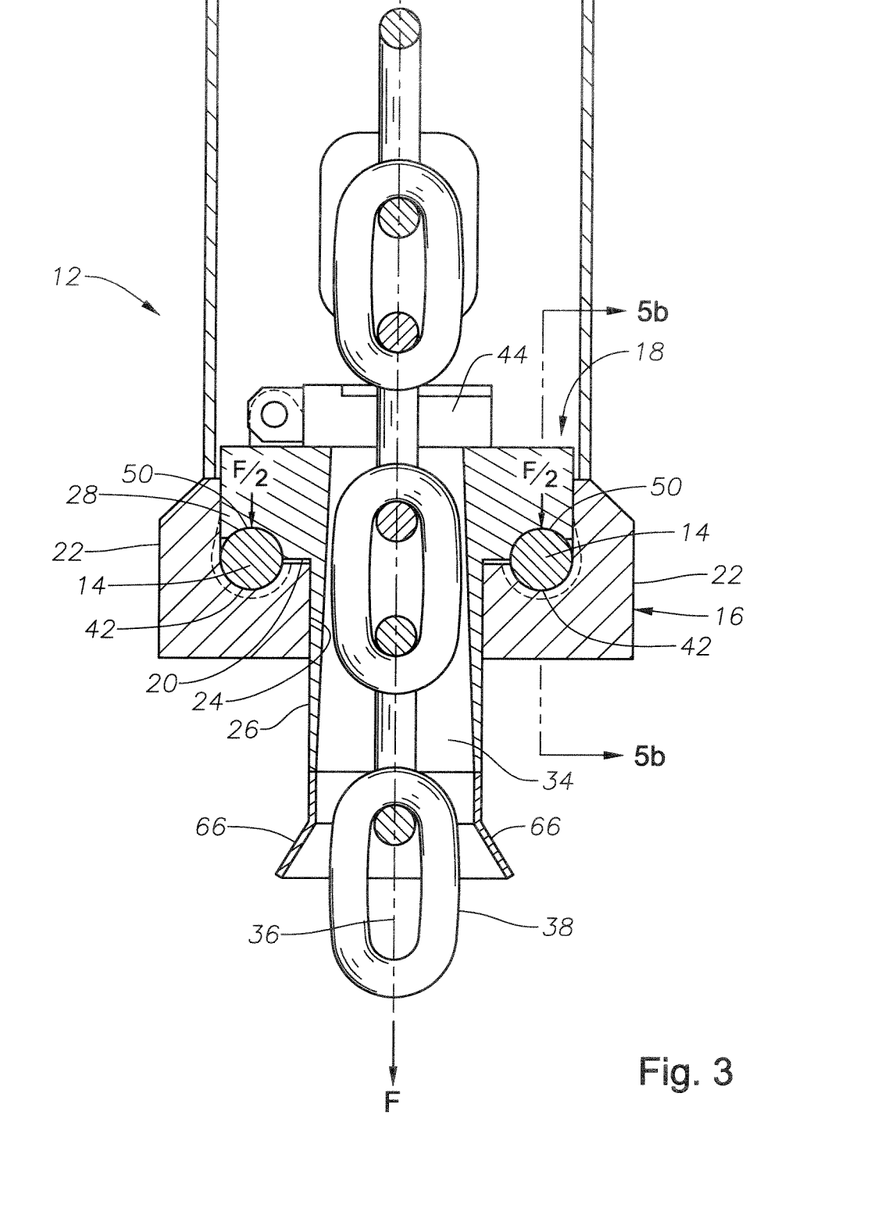
FIG. 3 is a side cross-sectional view of a chain stopper according to the invention taken along lines 3-3 of FIG. 2 illustrating load bearing pins.
Figure 4A:
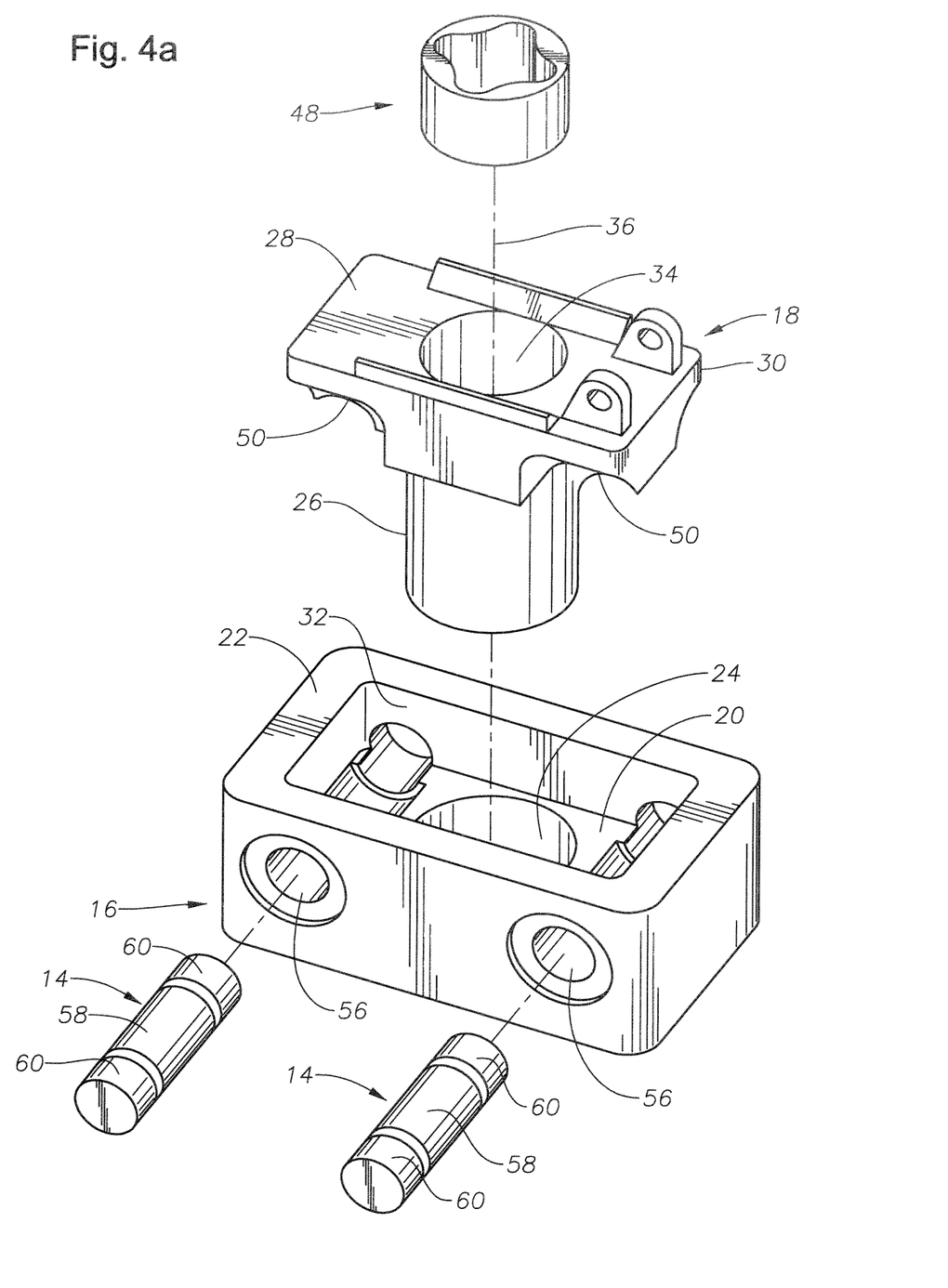
FIG. 4a is an exploded perspective view showing the base support, inner body, pins, and cruciform of a chain stopper according to the invention.
Figure 4B:
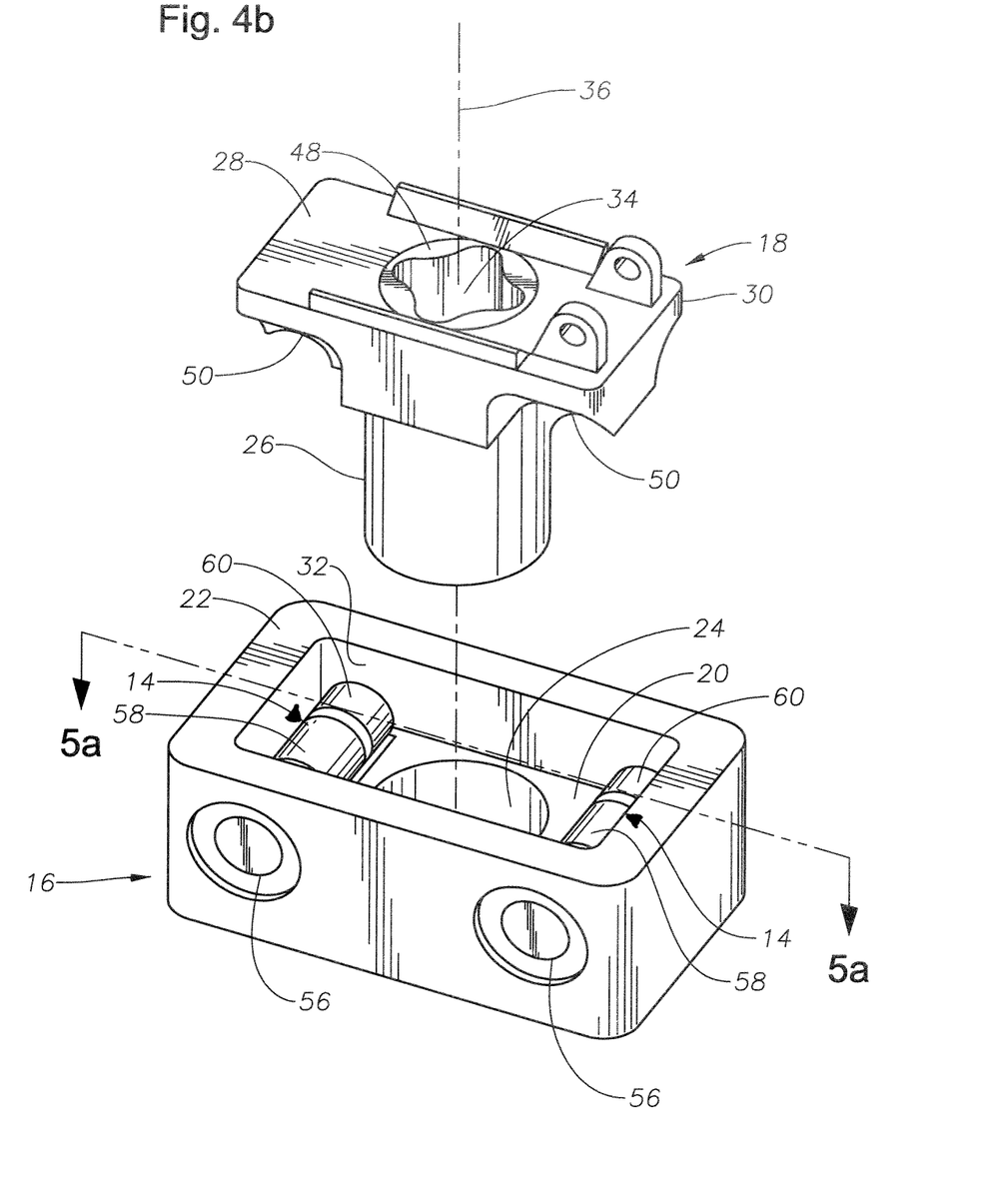
FIG. 4b is an exploded perspective view showing the base support, inner body, pins, and cruciform of the embodiment of FIG. 4a, with the pins inserted into the base support and the cruciform inserted in the inner body.

FIG. 3 shows a side cross-sectional view of a chainstopper assembly 12. The chainstopper assembly 12 includes a base support 16, an inner body 18, and pins 14. FIGS. 4a and 4b show exploded views of the base support 16, the inner body 18, and the pins 14 of the chainstopper assembly 12. The base support 16 is socket-shaped and has a bottom 20 and sides 22. A hole 24 is provided through the bottom 20 of the base support 16.

The inner body 18 of the chainstopper assembly 12 includes a shank portion 26 and a flange portion 28. The outer dimensions of the shank portion 26 correspond to the inner dimensions of the hole 24 in the base support 16 such that the hole 24 closely receives the shank portion 26. Similarly, the dimensions of the external surfaces 30 of the flange portion 28 correspond to the internal surfaces 32 of the sides 22 of the base support 16 such that the base support 16 closely receives the inner body 18. A fluted portion 66 (shown in FIGS. 2, 3 and 6) is attached to the end of the shank portion 26. The fluted portion 66 is attached after the shank portion 26 is inserted into the hole 24 of the base support 16.

As shown in FIGS. 3, 4a, and 4b, a passageway 34 extends through the inner body 18 and has a longitudinal axis 36 that corresponds to the longitudinal axis of the inner body 18. The passageway 34 is configured to allow passage of a chain 38. As shown in FIG. 3, a ratchet mechanism 44 is attached to the top of the inner body 18 adjacent the passageway 34. The ratchet mechanism 44 is configured to allow movement of the chain 38 in an upward direction away from the base support 16 while preventing movement in a downward direction. In addition, as shown in FIGS. 4a and 4b, the inner body 18 includes a cruciform 48 having an outer surface that corresponds to the inner surface of the passageway 34. The inner surface of the cruciform 48 is shaped to maintain the links of the mooring chain 38 in alternative orientations in the passageway 34 of the inner body 18.

Figure 5A:
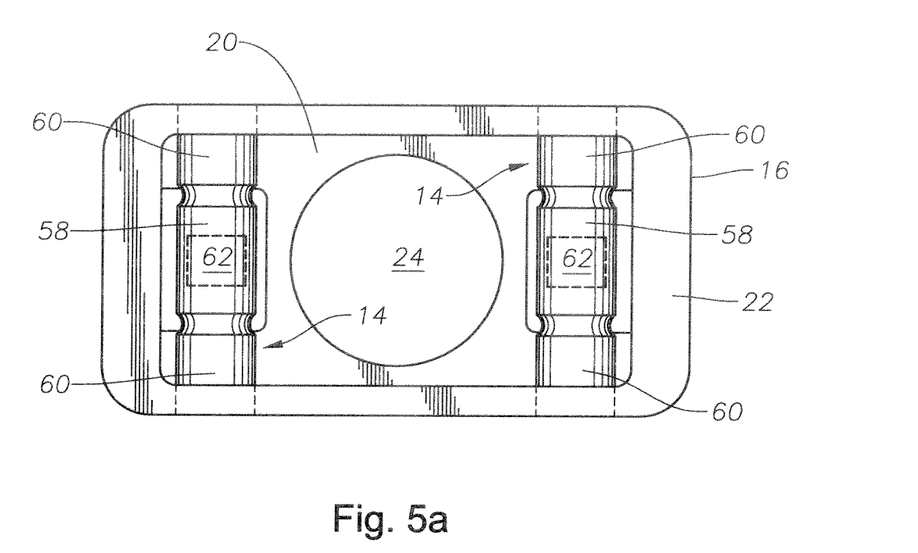
FIG. 5a is a top view of the base support and pins of FIG. 4b taken along lines 5a-5a of FIG. 4b.
Figure 5B:
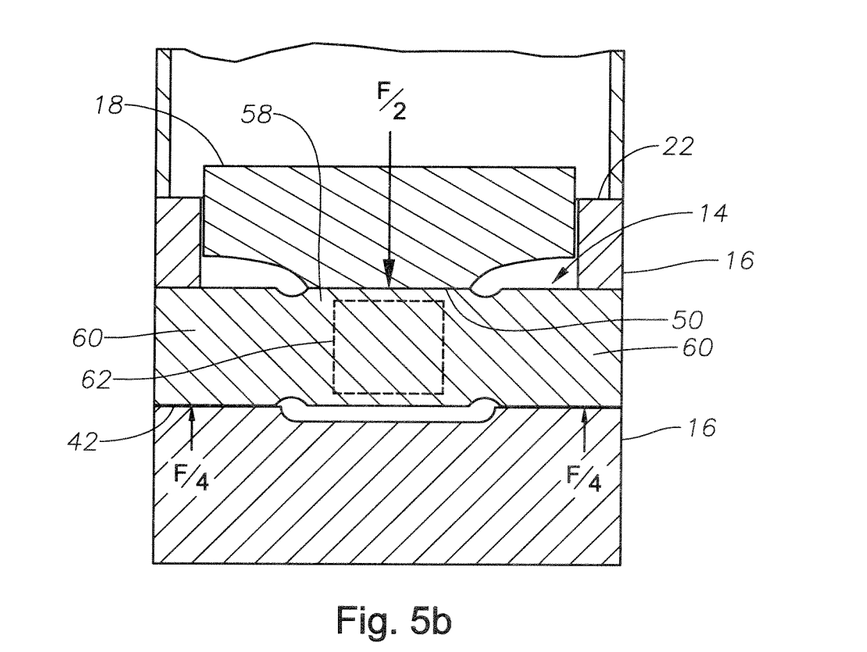
FIG. 5b is a cross-sectional view showing the pins and base support of the embodiment of FIG. 5a taken along the lines 5b-5b of FIG. 3.

The chainstopper assembly 12 further includes pins 14 positioned between the flange portion 28 of the inner body 18 and the bottom 20 of the base support 16. As shown in FIGS. 3 and 5b, the bottom 20 of the base support 16 includes curved contours 42 configured to accept pins 14. The flange 28 of the inner body 18 has similar contours 50 configured to conform to the top surface of the pins 14. As shown in FIG. 5a, the pins 14 traverse the base support 16 in a lateral direction. The pins 14 each have a center portion 58 and two side portions 60. Each pin 14 further includes strain gages 62 located at the center portion 58. The pins 14 are circular in radial cross-section.

As shown in FIG. 5b, the contours 42 of the base support 16 vary transversely across the base support 16, such that the base support 16 contacts pins 14 at the side portions 60 thereof but not at the center portion 58. Conversely, the contours 50 of the inner body 18 vary transversely across the inner body 18 such that the inner body 18 contacts each pin 14 at the center portion 58, but not at the side portions 60.

As shown in FIG. 4a, the sides 22 of base support 16 have openings 56 arranged and designed to allow passage of pins 14 therethrough. This arrangement allows for easy replacement of the pins in situ without disassembling the chainstopper assembly 12. This arrangement also allows calibration of the pins 14 at a remote location prior to installation in a mooring system, thereby saving the time and expense of calibrating the entire chain support assembly. After the pins 14 are inserted into the base support 16, removable covers (not shown) are attached to the outside of the base support 16 to cover the openings 56 and prevent the pins 14 from sliding laterally out of position.

In use, chain 38 is attached to chaintable 4 via chainstopper assembly 12 (as shown in FIG. 1). The chain 38 is tensioned, or loaded, as needed to moor a floating structure. As shown in FIG. 3, the tensioning of the chain 38 causes it to exert a force F in a direction toward the base support 16 and parallel to the axis 36 of the chain 38. Because the ratchet mechanism 44 prevents the chain from moving in a downward direction relative to the inner body 18, the force F is transferred from the chain 38 into the inner body 18. Pins 14 are positioned symmetrically on either side of the chain 38 between the inner body 18 and the base support 16. The force F is transferred through the pins 14 from the inner body 18 to the base support 16. Because the pins 14 are positioned symmetrically about the chain 38, the magnitude of the force F/2 transferred through each pin 14 is equal to half the tension force F applied to the chain. Moreover, because the pins 14 are positioned directly between the inner body 18 and the base support 16, the force F/2 passes directly through the pins.

Referring to FIG. 5b, there is shown the base support 16, inner body 18, and pins 14 of the invention while under load. As discussed above, the inner body 18 transfers a force F/2 in a downward direction to each pin 14. The inner body 18 contacts each pin 14 only at the center portion 58 thereof. Simultaneously, base support 16 exerts an equal and opposite force in an upward direction to keep the pin 14 in equilibrium. As discussed above, base support 16 contacts each pin 14 only at the two side portions 60. Thus, an upward force F/4, equal to half the downward force F/2, is exerted by base support 16 to each side portion 60 of each pin 14. The result of this configuration is that the center portion 58 deflects with respect to the side portions 60 upon application of the force F/2.

One or more strain gages 62 are located at the center portion 58 of each pin 14. The strain gages are inserted into the center portion 58 of each pin 14 through holes (not shown) extending radially into each pin 14. So configured, the strain gages 62 measure the deflection of each pin 14 as the force F/2 is applied. The amount of deflection of each pin 14 is directly related to the amount of force F/2 applied to each pin 14. The force F/2, in turn, is a component of the tension force F in the mooring chain 38. Thus, the strain gages 62 are positioned to provide direct measurement of the tension in each mooring chain 38. Each pin 14 preferably includes redundant strain gage bridges, thereby providing two circuits in each pin 14 for measuring tension. The method of placement and the structure and orientation of the strain gages is known in the art.

Figure 2:
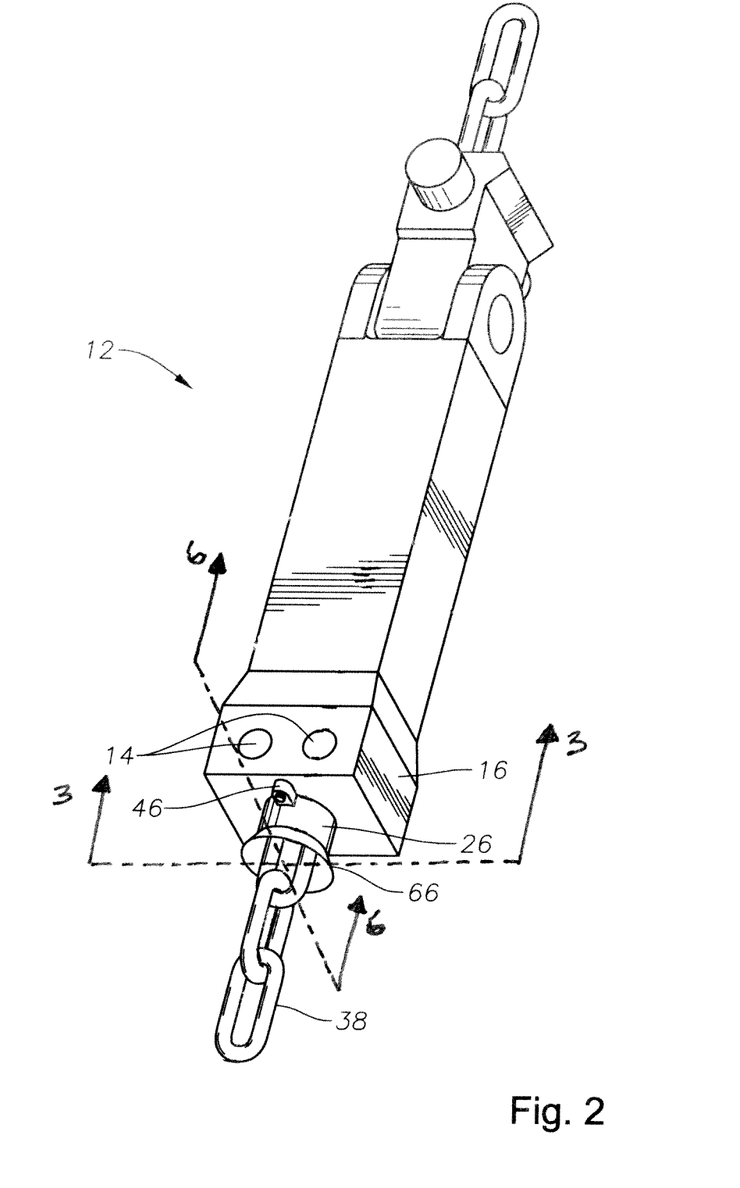
FIG. 2 is a perspective view of a chainstopper assembly according to the invention.
Figure 6:
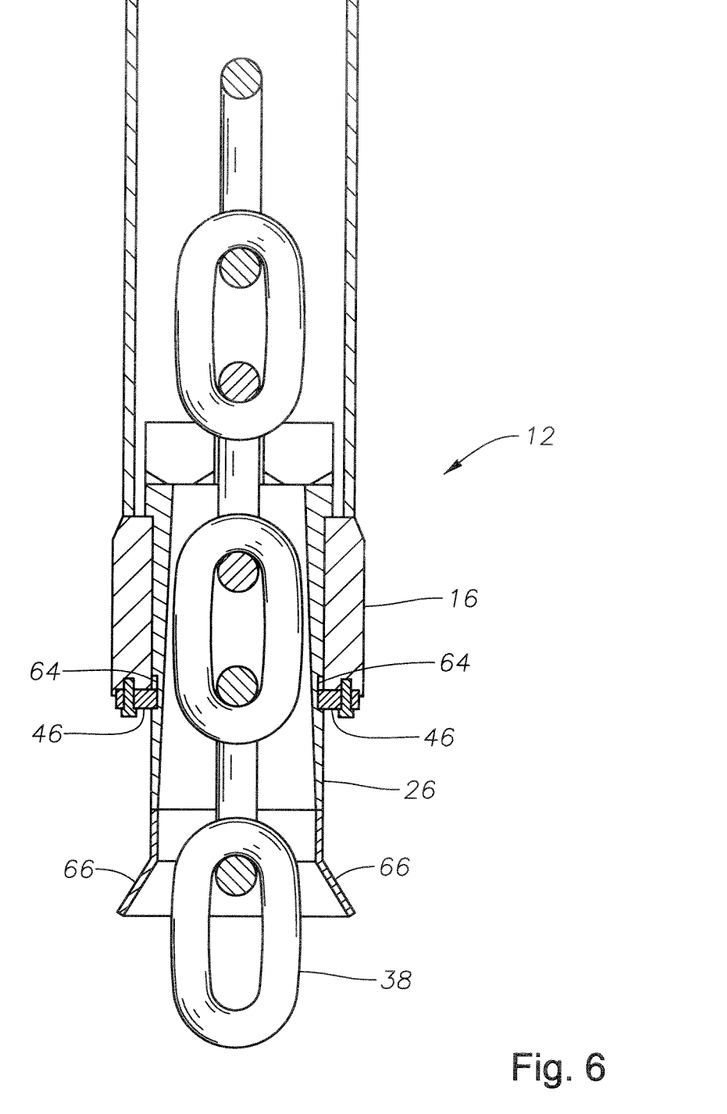
FIG. 6 is a side cross-sectional view of a chain stopper assembly taken along lines 6-6 of FIG. 2 according to the invention.

Referring now to FIG. 6, there is shown aside cross-sectional view of the chainstopper assembly 12 of FIG. 2 taken along lines 6-6, and further showing anti-lift keys 46. The anti-lift keys 46 are attached to the base support 16 and contact the shank portion 26 of the inner body 18 at slots 64. The slots 64 are recesses in the shank portion 26 that have a circumferential width and a longitudinal length with a top and a bottom. The width of each slot 64 is substantially equal to the width of a corresponding anti-lift key 46, such that when the anti-lift key 46 is inserted into the slot 64, the shank 26 cannot rotate circumferentially. When the inner body 18 is seated with the contours 50 contacting the pins 14 (as shown in FIG. 3), the bottom of the slot 64 contacts the bottom of the corresponding anti-lift key 46. In this way, the inner body 18 is restrained from moving upward with respect to the base support 16. Conversely, the top of each slot 64 is spaced from the top of the corresponding anti-lift key 46 such that the inner body 18 can deflect relative to the base support 16 when aloud is applied to the chain 38. Accordingly, the anti-lift key restrains movement of the inner body rotationally and in an upward direction, but does not interfere with downward deflection of the inner body 18 as the pins 14 measure load.

What is claimed is:
1. An arrangement for measuring tension in mooring chains (38) connected to a floating structure (6), comprising:
    a chain stopper (12) having a first portion (16) and a second portion (18), said first portion (16) having a first load bearing surface (42) and said second portion (18) having a second load bearing surface (50); and at least one pin (14) having at least one strain gage (62) for measuring loads, said pin laterally traversing said chain stopper (12) between said first and second load bearing surfaces (50, 42);

whereby, upon application of a load to said chain stopper (12), said at least one pin (14) is positioned in the load path, wherein said at least one pin (14) has a center portion (58) and two side portions (60), and further comprising at least one strain gage (62) positioned at said center portion (58), wherein said second load bearing surface (50) contacts said at least one pin (14) only at said center portion (58), and said first load bearing surface contacts said at least one pin (14) only at said side portion (60), and wherein said second portion (18) includes a slot (64) in the outer surface thereof, the arrangement further comprising:

at least one anti-lift key (46) attached to said first portion (16) and engaged with said slot (64) of said second portion;

wherein said slot (64) and said anti-lift key (46) are arranged and dimensioned to restrain upward movement, while allowing downward movement of said second portion (18) relative to said first portion (16) and to prevent rotation of said second portion (18) with respect to said first portion (16).

2. The arrangement of claim 1, wherein
said at least one pin (14) has a circular radial cross-section.

3. The arrangement of claim 1, wherein
two pins (14) traverse said chain stopper (12) between said first and second load bearing surfaces (50, 42).

4. The arrangement of claim 3, wherein
each pin (14) includes redundant strain gage bridges, thereby providing four circuits for measuring loads.

5. The arrangement of claim 1, wherein
said first portion (16) includes at least one hole (56) arranged and designed to accept lateral insertion of said at least one pin (14) without disassembling the arrangement.

6. The arrangement of claim 1, wherein
said second portion (18) has a longitudinal axis (36) and defines a passageway (34), said passageway (34) extending through said second portion (18) along said longitudinal axis (36) and configured to receive a mooring chain (38).

7. The arrangement of claim 6, further comprising
a ratchet mechanism (44) attached to said second portion (18) adjacent said passageway (34) and configured to allow unidirectional movement of the mooring chain (38).

8. The arrangement of claim 6, further comprising:
a cruciform (48) arranged and designed to fit within said passageway (34) and shaped to maintain the links of the mooring chain (38) in alternative orientations in said passageway (34).

9. An arrangement for measuring anchor chain load, comprising:
a base support (16) having a base support load surface (42);
an inner body (18) having an inner body load surface (50) and configured to be inserted longitudinally within said base support (16), said base support having transverse openings (56) in its sides; and
at least one load-measuring pin (14) placed between said base support load surface (42) and said inner body load surface (50), wherein said inner body (18) includes a slot (64) in the outer surface thereof, the arrangement further comprising:
at least one anti-lift key (46) attached to said base support and engaged with said slot (64) of said inner body (18);
wherein said slot (64) is configured to restrain upward movement, while allowing downward movement of said inner body (18) relative to said base support (16);
and wherein said slot (64) is configured to prevent rotation of said inner body (18) relative to said base support (16).

10. The arrangement of claim 9, wherein
said at least one pin (14) has a center portion (58) and two side portions (60), and further comprising at least one strain gage (62) positioned at said center portion (58).

11. The arrangement of claim 10, wherein
said inner body load surface (50) contacts said at least one pin (14) only at said center portion (58), and said base support load surface (42) contacts said at least one pin (14) only at said side portions (60).

12. The arrangement of claim 9, wherein
two load-measuring pins (14) are placed between said base support load surface (42) and said inner body load surface (50).

13. The arrangement of claim 9, wherein
said at least one load-measuring pin (14) has a circular radial cross-section.

14. A load measuring arrangement, comprising:
a base support (16) having a base support load surface (42);
an inner body (18) having an inner body load surface (50), said inner body including a slot (64) in said outer surface thereof;
at least one pin (14) configured to measure load and placed between said base support load surface (42) and said inner body load surface (50); and
at least one anti-lift key (46) attached to said base support (16) and engaged with said slot (64) of said inner body (18);
wherein said slot (64) is configured to restrain upward movement, while allowing downward movement of said inner body (18) relative to said base support (16);
wherein said slot (64) is configured to prevent rotation of said inner body (18) relative to said base support (16).

15. The load monitoring arrangement of claim 14, wherein
said base support (16) defines openings (56) arranged and designed to accept lateral insertion of said at least one pin (14) between said base support load surface (42) and said inner body load surface (50) without disassembling said load monitoring arrangement.

16. The arrangement of claim 14, wherein
two pins (14) are placed between said base support load surface (42) and said inner body load surface (50).

17. The arrangement of claim 16, wherein
each pin (14) includes redundant strain gage bridges, thereby providing four circuits for measuring shear loads.

18. The arrangement of claim 14, wherein
said at least one pin (14) has a center portion (58) and two side portions (60), and further comprising at least one strain gage (62) positioned at said center portion (58).

19. The arrangement of claim 18, wherein
said inner body load surface (50) contacts said at least one pin (14) only at said center portion (58), and said base support load surface (42) contacts said at least one pin (14) only at said side portions (60).

20. The arrangement of claim 14, wherein
said at least one pin (14) has a circular radial cross-section.

* * * * *